United States Patent
Kim (10) Patent No.: US 9,269,128 B2
(45) Date of Patent: Feb. 23, 2016

(54) METHOD FOR REDUCING NOISE IN MEDICAL IMAGE

(75) Inventor: Jong Hyo Kim, Seoul (KR)

(73) Assignee: SNU R&DB FOUNDATION (KR)

( * ) Notice: Subject to any disclaimer, the term of this patent is extended or adjusted under 35 U.S.C. 154(b) by 0 days.

(21) Appl. No.: 14/402,800

(22) PCT Filed: May 23, 2012

(86) PCT No.: PCT/KR2012/004069
§ 371 (c)(1),
(2), (4) Date: Nov. 21, 2014

(87) PCT Pub. No.: WO2013/176310
PCT Pub. Date: Nov. 28, 2013

(65) Prior Publication Data
US 2015/0131885 A1    May 14, 2015

(30) Foreign Application Priority Data
May 23, 2012  (KR) .................. 10-2012-0054557

(51) Int. Cl.
| | | |
|---|---|---|
| G06K 9/00 | (2006.01) | |
| G06T 5/00 | (2006.01) | |
| G06T 5/20 | (2006.01) | |
| A61B 6/00 | (2006.01) | |

(52) U.S. Cl.
CPC . *G06T 5/002* (2013.01); *G06T 5/20* (2013.01); *A61B 6/5258* (2013.01); *G06T 2207/10072* (2013.01); *G06T 2207/10116* (2013.01); *G06T 2207/20024* (2013.01); *G06T 2207/20182* (2013.01); *G06T 2207/30004* (2013.01)

(58) Field of Classification Search
CPC .................................. G06T 5/00; G06T 5/20
USPC ........................................................ 382/132
See application file for complete search history.

(56) References Cited

U.S. PATENT DOCUMENTS

| | | | |
|---|---|---|---|
| 5,641,596 A * | 6/1997 | Gray et al. ....................... | 430/21 |
| 6,314,160 B1 | 11/2001 | Dhawale et al. | |
| 7,660,481 B2 | 2/2010 | Schaap et al. | |
| 2004/0027469 A1* | 2/2004 | Tsuruoka ....................... | 348/241 |
| 2004/0120597 A1* | 6/2004 | Le Dinh ....................... | 382/261 |
| 2008/0007747 A1 | 1/2008 | Chinen et al. | |

FOREIGN PATENT DOCUMENTS

| | | |
|---|---|---|
| JP | 2001238869 | 9/2001 |
| JP | 2008142297 | 6/2008 |
| KR | 1020010041909 | 5/2001 |

OTHER PUBLICATIONS

International Search Report—PCT/KR2012/004069 dated Dec. 28, 2012.

* cited by examiner

*Primary Examiner* — Gregory F Cunningham
(74) *Attorney, Agent, or Firm* — Cantor Colburn LLP (57) ABSTRACT

There is provided a method of reducing noise in a medical image while maintaining structure characteristics within the medical image. The method of reducing noise in the medical image includes: a step of estimating the amount of noise at each pixel by using a look-up table that previously stores physical properties of an image capturing device; a step of calculating a structure direction and a signal coherence at each pixel; a step of performing anisotropic smoothing by using an anisotropic smoothing filter kernel that reflects the structure direction and the signal coherence; and a step of obtaining a structure direction and a signal coherence from an image on which the anisotropic smoothing is performed, obtaining an anisotropic smoothing filter kernel that reflects the obtained structure direction and the signal coherence, and performing filtering that reflects statistical properties of the estimated amount of noise.

13 Claims, 8 Drawing Sheets

METHOD FOR REDUCING NOISE IN MEDICAL IMAGE

TECHNICAL FIELD

The embodiments described herein pertain generally to a method of reducing noise in a medical image while maintaining structure properties in the medical image, and more particularly, to a method of reducing noise of a medical image with which it is possible to increase image quality by selectively suppressing the noise while effectively preserving an anatomical structure component of the medical image by estimating the amount of noise in a position of each pixel, extracting a signal structure direction and a signal coherence at each pixel, obtaining a filter kernel that reflects the signal structure direction and signal coherence, and performing convolution that reflects noise statistics.

BACKGROUND

In modern medicine, medical images captured by X-ray irradiation, CT and MRI play important roles for diagnosing patients or making decision in treating the patients. Accordingly, obtaining high-quality images with less noise is necessary in medical imaging examinations. A medical image is produced by physical energy in which image signals are generated through the reaction of the physical energy with the body and detected by a detector. So, in the medical image obtaining procedure, noise is unavoidably included in the image due to slight variations in an energy generating source and energy distribution in space as well as the occurrence of thermodynamic noise within the detector. Especially in X-rap and CT examinations that use ionizing radiation, in order to reduce potential harm due to radiation exposure, it is necessary to reduce a radiation dose exposure when capturing the medical image. However, a reduction of the radiation dose causes an increased noise level in the medical image.

An important step in imaging examination chain is the application of appropriate post processing technique which reduces the image noise generated at the time of image capture, in order to increase the value of clinical utilization of the medical image.

However, a general method of reducing noise in the field of image processing is primarily focused to enhance visual comfort. For this reason, mechanisms that prevent the degradation of structural properties within the image caused by the noise reduction procedure are not sufficiently provided. The degradation of an important anatomical structure or lesion shape caused by the noise reduction procedure may lead to an error in imaging diagnosis, which may in turn bring about a serious consequence in patient care. Accordingly, the noise reduction method of the medical image needs to have specially tuned mechanisms unlike those techniques used in a general application field.

DISCLOSURE OF THE INVENTION

Problems to be Solved by the Invention

In view of the foregoing, example embodiments provide a method of selectively removing the noise component in a medical image while preserving structure properties. More particularly, example embodiments also provide a method of performing filtering for selectively suppressing noise while preserving structure properties by estimating the amount of noise at each pixel within an image based on a look-up table that is previously stored according to a capturing condition, and extracting structure properties from each pixel of the image, and performing anisotropic smoothing filtering that reflects the structure properties.

Means for Solving the Problems

In an aspect of example embodiments, a method of reducing noise in a medical image includes: a step of estimating the amount of noise at each pixel position of an image by using a look-up table that is previously stored; a step of extracting a first signal structure direction and a first signal coherence in the position of each pixel; a step of obtaining a first anisotropic smoothing filter kernel that reflects the extracted signal structure direction and the signal coherence; a step of obtaining an anisotropic-smoothed intermediate image by performing filtering using the first anisotropic smoothing kernel; and a step of extracting a second signal structure direction and a second signal coherence for each pixel of the anisotropic-smoothed intermediate image, and obtaining a second anisotropic filter kernel that reflects the second signal structure direction and the second signal coherence, and perform filtering on an original image by applying an additional weight that reflects the estimated amount of noise at each pixel position to surrounding pixels within a range of the filter kernel.

Here, the previously stored look-up table may be a two-dimensional look-up table that has two terms including a radiation dose for an object during irradiation of X-ray and a signal average value for each pixel in an image, and may provide a noise standard deviation at each pixel by inputting a radiation dose value which is provided from an image capturing device and a signal average value at each pixel in the image.

When the radiation dose value is not provided from the image capturing device, the radiation dose value may be generated by referring to the look-up table that previously stores information including an X-ray tube voltage, the product of a tube current and radiation time, a distance between an X-ray focal point and a detector, and a used X-ray energy filter.

In the step of extracting the signal structure direction and the signal coherence at each pixel position, the signal structure direction may be determined as a vertical direction of a gradient vector that is normalized at each pixel, and the signal coherence may be determined by obtaining absolute values of gradient values of the normalized gradient vector and a vertical direction vector of the gradient vector and dividing a difference value between the absolute values of the gradient values by the sum of the absolute values.

In the step of extracting the signal structure direction and the signal coherence at each pixel position, the signal structure direction may be determined as a second eigenvector of the Hessian matrix at each pixel, and the signal coherence may be determined by obtaining absolute values of two eigenvalues of the Hessian matrix and dividing a difference value between the absolute values of the two eigenvalues by the sum of the absolute values.

In the step of extracting the signal structure direction and the signal coherence at each pixel position, the signal structure direction and the signal coherence may be determined as the signal structure direction and the signal coherence when a ratio of an absolute value of a gradient value obtained at each pixel to an absolute value of a first eigenvalue of the Hessian matrix is obtained and the obtained ratio is greater than a predetermined threshold value, and the signal structure direction and the signal coherence may be determined as the signal structure direction and the signal coherence when the ratio is smaller than the predetermined threshold value.

In the step of obtaining the anisotropic smoothing filter kernel that reflects the signal structure direction and the signal coherence that are extracted at each pixel, a kernel that follows a two-dimensional anisotropic Gaussian function using the structure direction and the signal coherence may be obtained, and lengths of a major axis and a minor axis of the anisotropic Gaussian function may be respectively determined as a size of the kernel and a value obtained by multiplying the size of the kernel and the signal coherence, and a rotation angle of the anisotropic Gaussian function may be determined as the structure direction.

In the step of obtaining the anisotropic-smoothed intermediate image by performing filtering using the first anisotropic smoothing filter kernel, anisotropic smoothing filtering may be repeatedly performed by the number of times that is determined by multiplying a predetermined proportional coefficient and the sum of the estimated amounts of noise at respective pixels in the image.

In the step of applying the additional weight that reflects the estimated amount of noise in the position of each pixel to the surrounding pixels within the range of the filter kernel, a ratio may be obtained by dividing an absolute value of a difference value between a pixel value of the anisotropic-smoothed intermediate image at central pixel of the kernel and a pixel value of the original image at surrounding pixel by the estimated amount of noise, and a value obtained by dividing the sum of the ratio and a predetermined constant β by 1 may be applied as a weight for the surrounding pixel.

In the step of applying the additional weight that reflects the estimated amount of noise at each pixel position to the surrounding pixels within the range of the filter kernel, a value of the Gaussian function in which the estimated amount of noise at central pixel of the kernel is set as a standard deviation, the pixel value of the anisotropic-smoothed intermediate image is set as an average value, and the pixel value of the original image at surrounding pixel is set as a variable may be obtained, and the obtained value may be set as a weight for the surrounding pixel.

In the step of performing filtering on the original image by applying the additional weight that reflects the estimated amount of noise at each pixel position to the surrounding pixels within the range of the filter kernel and outputting the filtered image as a final output, the filtering may be repeatedly performed by the number of times determined by multiplying a predetermined proportional coefficient and the sum of the estimated amounts of noise for the respective pixels in the image, which are obtained from the original image, and a value obtained by multiplying a predetermined reduction coefficient and the estimated amount of noise of the preceding filtering may be used as the estimated amount of noise at each pixel whenever the filtering is repeated.

In the step of performing filtering on the original image by applying the additional weight that reflects the estimated amount of noise at each pixel position to the surrounding pixels within the range of the filter kernel and outputting the filtered image as a final output, a small amount of noise existing in a natural state may be included in the original image by mixing a filtering result value $I_{sn}[x, y]$ at each pixel and a pixel value $I[x, y]$ of the original image by a predetermined ratio.

Effect of the Invention

In accordance with the example embodiments, the method of reducing noise in a medical image may provide two unique properties for removing noise. First, the amount of noise at each pixel in a medical image is effectively estimated based on a physical principle in a procedure of obtaining the medical image, and the estimated amount of noise is used to remove the noise. If the amount of noise for each area is estimated, strong smoothing may be performed on a pixel region that has a large amount of noise, and weak smoothing may performed on a pixel region that has a small amount of noise. Accordingly, it is possible to prevent image quality from being deteriorated due to unnecessarily and excessively smoothing.

Second, structure properties are extracted at each pixel of the image, and anisotropic smoothing filtering that reflects the structure properties is performed. If the anisotropic smoothing filtering is performed, it is possible to preserve anatomical structure properties of the image more effectively. It is possible to suppress the noise while preserving the structure properties by utilizing the two unique properties for removing noise.

MODE FOR CARRYING OUT THE INVENTION

Hereinafter, preferred example embodiments will be described in detail with reference to the accompanying drawings. Prior to the description, terms and words used in the present specification and claims should not be interpreted as being limited to general meanings or dictionary meanings, but should be interpreted as having meanings and concepts relevant to the technical spirit of the present invention based on the rule according to which an inventor can appropriately define the concept of the term to describe the best method he or she knows for carrying out the invention.

Accordingly, the example embodiments described in the present specification and the configurations illustrated in the drawings are merely the most preferred example embodiments of the present disclosure, and do not wholly represent the technical sprit of the present disclosure. Therefore, it should be appreciated that various modifications and equivalents to these example embodiments are possible at the time of filing the present application.

Figure 1:
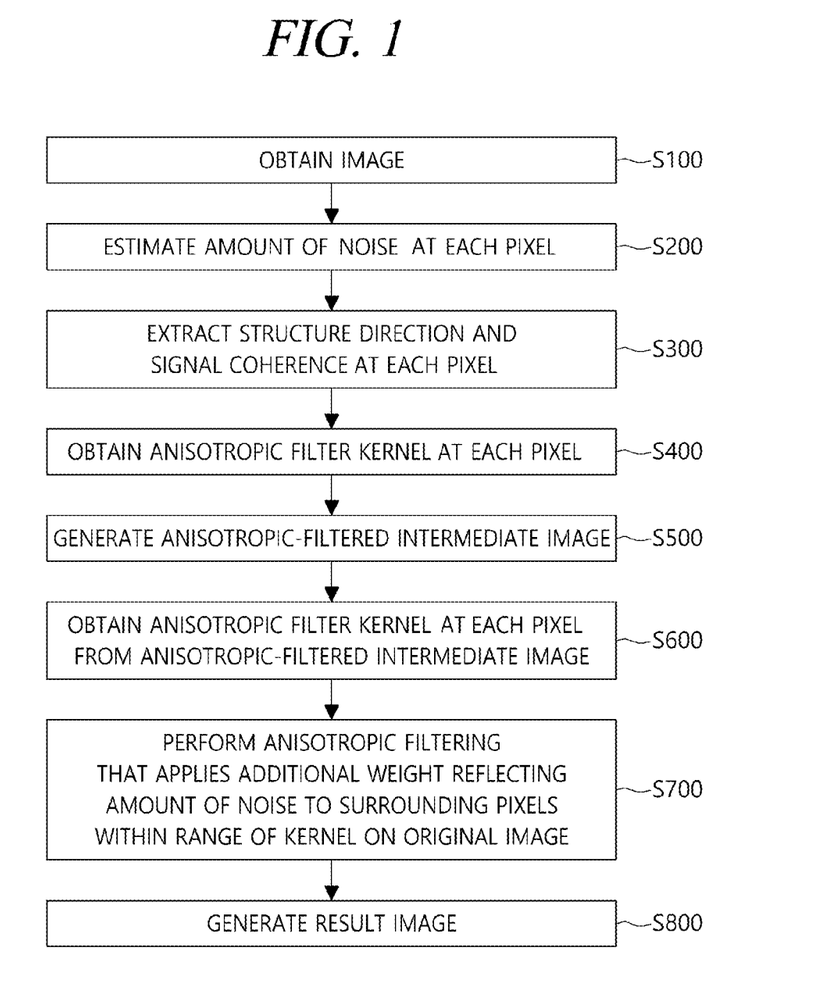
FIG. 1 shows an example processing flow of processing image data, in accordance with various embodiments described herein.

FIG. 1 shows an example processing flow of processing image data, in accordance with various embodiments described herein. The processing flow includes step S100 of obtaining an image, step S200 of estimating an amount of noise, step S300 of extracting a structure direction and a signal coherence, step S400 of obtaining an anisotropic filter kernel, step S500 of generating an anisotropic-filtered intermediate image, step S600 of obtaining an anisotropic filter kernel for each pixel from the anisotropic-filtered intermediate image, step S700 of performing, on an original image, anisotropic filtering to which a weight that reflects the amount of noise is applied, and step S800 of generating a result image. The respective steps will be described in detail below.

Figure 2:
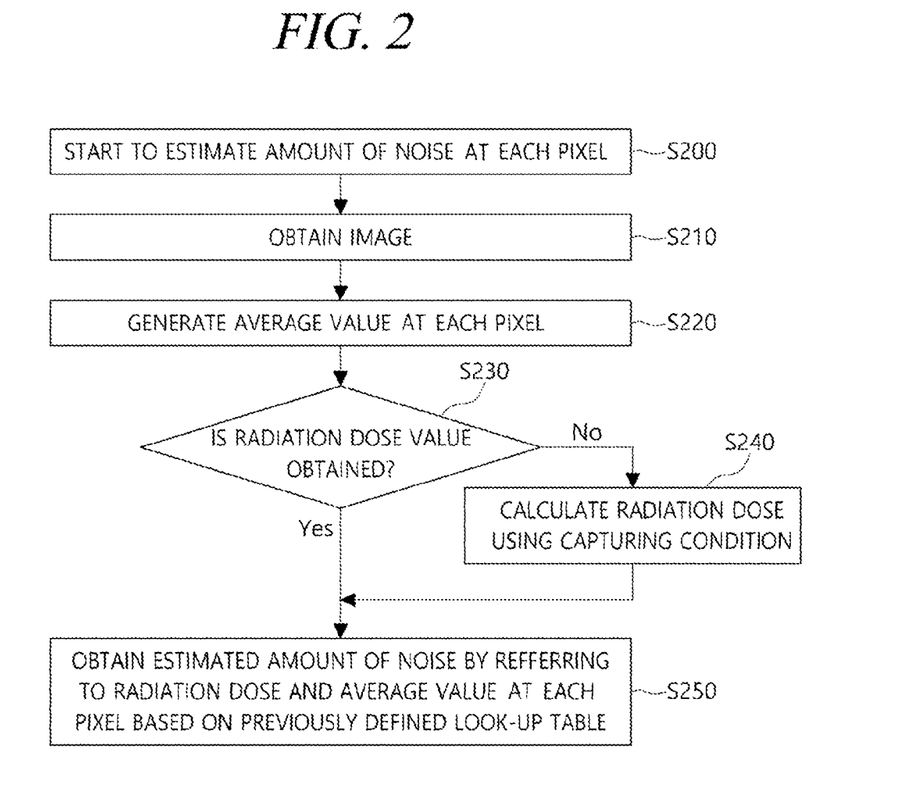
FIG. 2 shows an example processing flow of processing data in a step of estimating an amount of noise at each pixel, in accordance with various embodiments described herein.

FIG. 2 shows an example processing flow of processing data in a step of estimating an amount of noise at each pixel. Specifically, the amount of noise at each pixel is estimated by collectively referring to a radiation dose during capturing an image, obtained image data, and a noise property look-up table associated with a capturing device, which is stored in advance. By finding information on the amount of noise at each pixel, it is possible to avoid noise from being suppressed unnecessarily and excessively in the later noise suppressing process. As a result, it is possible to prevent image quality from being deteriorated in a smoothing process.

In an image device that generates an image such as an optical image or an X-ray image that is generated by photons, noise may be caused in the image as follows. That is, the noise may be caused by a statistical distribution of the photons, and may be caused by an internal electronic circuit of a system. It is known that the statistical distribution of the photons incident into a single pixel follows the Poisson distribution, and in this case, a standard deviation of pixel values is determined by a square root of the number of photons that are averagely incident into each pixel. However, noise that does not follow the Poisson distribution is added to pixel values of an actual obtained image in an internal electronic circuit of an image detector, and the image including the noise is output. In this way, there may be a complicated relationship in which a combination of thermal noise of an electronic device and interference noise by X-ray energy acts on the image.

In order to more simply estimate the amount of noise determined by such complicated factors, a noise amount look-up table is used in the example embodiment. The noise amount look-up table used in the example embodiment is a two-dimensional table. In this table, the first item indicates an X-ray radiation dose for a target object, and the second item indicates an average value of image signals for each pixel. The X-ray radiation dose is a value that represents a dose of radiation incident onto the target object from an X-ray generator during capturing an image. The X-ray radiation dose may be obtained by a radiation dose meter that is built in the capturing device, or may be replaced with a value that is measured in advance under a capturing condition where image capturing has been frequently performed. In the example embodiment, after the noise amount look-up table is previously generated for the capturing device through an experiment, a noise amount estimation value $\sigma_n[x, y]$ at each position $[x, y]$ within an image is obtained using this look-up table during actual capturing.

The second step in the example embodiment is a step of estimating the structure direction and the signal coherence for each pixel. The structure direction and the signal coherence at each pixel are estimated using a gradient vector of signal strength and an eigenvector of the Hessian matrix $H[x, y]$ in each pixel position. By finding the structure direction and the signal coherence for each pixel, it is possible to selectively reduce only a noise component while preserving internal structure properties of the image by performing smoothing using the structure direction and the signal coherence in the later noise suppressing process.

In the example embodiment, the structure direction refers to a traveling direction of a structure, and the signal coherence refers to a degree of clarity of the structure direction of the signal. A vector $D_g[x, y]$ that represents a traveling direction of a structure with an orientation may be obtained as Equation (2) by obtaining a gradient vector $G[x, y]$ expressed by Equation (1) in a given pixel position $[x, y]$, normalizing the obtained gradient vector by Equation (1-1), and obtaining a vertical direction of the normalized gradient vector. A signal coherence $C_g[x, y]$ may be obtained from a signal gradient value $\mu_1$ with the normalized gradient vector and a signal gradient value $\mu_2$ of its perpendicular direction, and a preferred example of the signal coherence is expressed as Equation (3).

$$G[x, y] = \begin{bmatrix} \frac{\Delta I[x, y]}{\Delta x} \\ \frac{\Delta I[x, y]}{\Delta y} \end{bmatrix} \quad \text{Equation (1)}$$

$$G_n[x, y] = \frac{1}{|G[x, y]|} \begin{bmatrix} \frac{\Delta I[x, y]}{\Delta x} \\ \frac{\Delta I[x, y]}{\Delta y} \end{bmatrix} \quad \text{Equation (1-1)}$$

$$D_g[x, y] = \frac{1}{|G[x, y]|} \begin{bmatrix} \frac{-\Delta I[x, y]}{\Delta y} \\ \frac{\Delta I[x, y]}{\Delta x} \end{bmatrix} \quad \text{Equation (2)}$$

$$\mu_1 = I[x + G_n x, y + G_n v] - I[x, y]$$
$$\mu_2 = I[x + D_g x, y + D_g v] - I[x, y]$$

$$C_g[x, y] = \frac{|\mu_1| - |\mu_2|}{|\mu_1| + |\mu_2|} \quad \text{Equation (3)}$$

Meanwhile, when there is a thin linear structure within an image, since magnitude of a gradient at the center of a line segment becomes '0,' even though the structure travels, the direction thereof may not be represented. In this case, first and second eigenvalues $\lambda_1$ and $\lambda_2$ and eigenvectors $V_1[x, y]$ and $V_2[x, y]$ corresponding thereto are obtained from the Hessian matrix $H[x, y]$ expressed by Equation (4), and then the direction thereof expressed by Equation (5) may be obtained as the eigenvector corresponding to the eigenvalue of a smaller value. In this case, the signal coherence $C_h[x, y]$ may be obtained as Equation (6) by using the two eigenvalues $\lambda_1$ and $\lambda_2$ obtained from the Hessian matrix.

$$H[x, y] = \begin{bmatrix} \frac{\partial^2 I[x, y]}{\partial x \partial x} & \frac{\partial^2 I[x, y]}{\partial x \partial y} \\ \frac{\partial^2 I[x, y]}{\partial x \partial y} & \frac{\partial^2 I[x, y]}{\partial y \partial y} \end{bmatrix} \quad \text{Equation (4)}$$

$$D_h[x, y] = \begin{bmatrix} V_1(x, y) & \text{if } |\lambda_2| > |\lambda_1| \\ V_2(x, y) & \text{else} \end{bmatrix} \quad \text{Equation (5)}$$

$$C_h[x, y] = \frac{|\lambda_1| - |\lambda_2|}{|\lambda_1| + |\lambda_2|} \qquad \text{Equation (6)}$$

Figure 3:
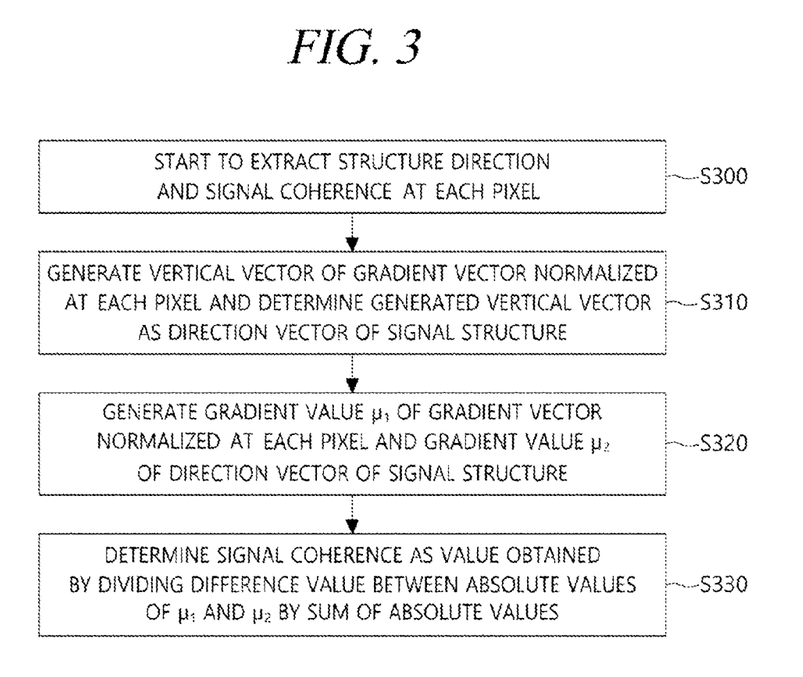
FIG. 3 shows an example processing flow of determining a structure direction and a signal coherence for an image that has no linear structure therein or is not important, in accordance with various embodiments described herein.
Figure 4:
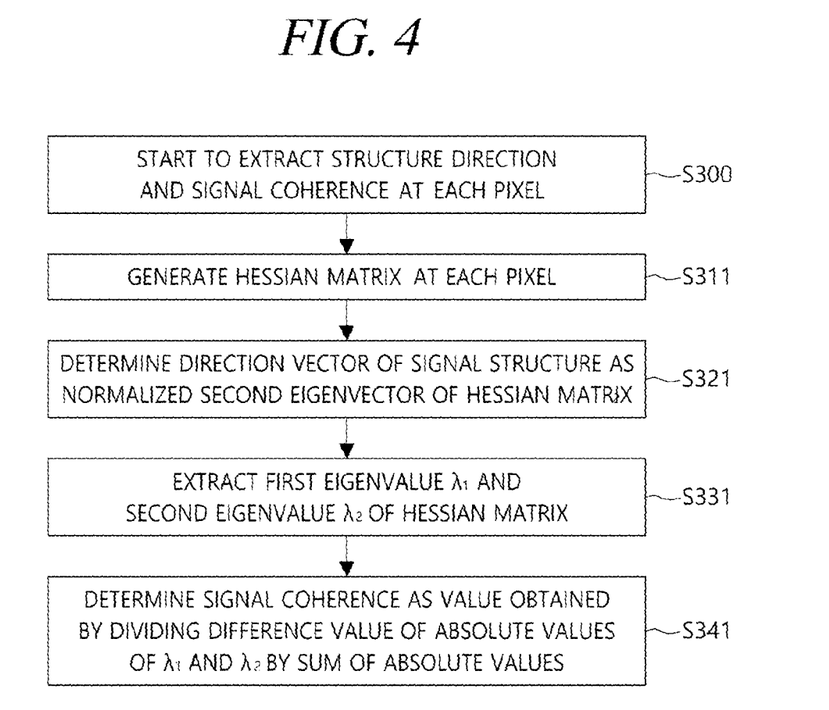
FIG. 4 shows an example processing flow of determining a structure direction and a signal coherence for an important image that has multiple linear structures therein, in accordance with various embodiments described herein.
Figure 5:
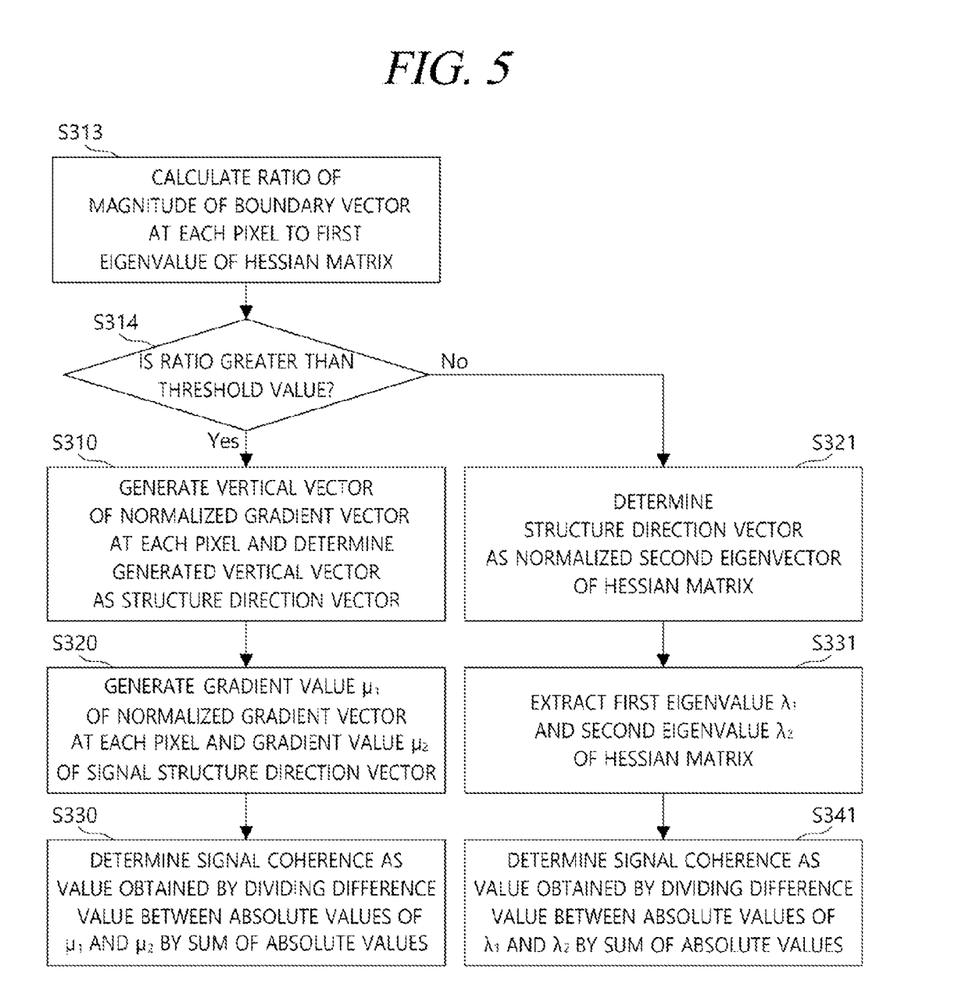
FIG. 5 shows an example processing flow of determining a structure direction and a signal coherence for an image that has a linear structure therein and has an intermediate importance, in accordance with various embodiments described herein.

FIGS. 3 to 5 show processing flows depending on importance of an image and whether there is a linear structure or not as described below. In the example embodiment, the structure direction and the signal coherence at each pixel may be obtained in various manners depending on the importance of the image and whether there is a linear structure or not. More specifically, for an image that has no linear structure or is not important, the structure direction and the signal coherence are obtained by Equations (2) and (3). For an image that has plural linear structures, the structure direction and the signal coherence are obtained by Equations (5) and (6). For an image that has an intermediate importance, the structure direction and the signal coherence are obtained by Equations (7) and (8).

$$D_{g+h}[x, y] = \begin{bmatrix} D_g(x, y) & \text{if } \frac{|G(x, y)|}{\lambda_1} > T \\ D_h(x, y) & \text{else} \end{bmatrix} \qquad \text{Equation (7)}$$

$$C_{g+h}[x, y] = \begin{bmatrix} C_g(x, y) & \text{if } \frac{|G(x, y)|}{\lambda_1} > T \\ C_h(x, y) & \text{else} \end{bmatrix} \qquad \text{Equation (8)}$$

The third step in the example embodiment is a step of performing smoothing filtering by using the structure direction and the signal coherence at each pixel. In this step, by selecting an anisotropic filter kernel that reflects the obtained structure direction and the signal coherence for each pixel to perform filtering, smoothing is performed to preserve properties of the structure.

As the anisotropic filter kernel that reflects the structure direction and signal coherence, any kernel may be used as long as a kernel gives a higher weight to pixels located in the structure direction than pixels located in other directions and has a difference between lengths of a major axis and a minor axis of the filter kernel depending on the signal coherence. However, in the example embodiment, a two-dimensional anisotropic Gaussian filter kernel is used as a preferred example. Equation (9) represents a two-dimensional anisotropic Gaussian function where a length of a major axis is $\sigma_x$, a length of a minor axis is $\sigma_x$, and an angle is $\theta$. From Equation (9). It is possible to appropriately generate a filter kernel that may express anisotropy by changing the length of the major axis and the length of the minor axis, may express a degree of the anisotropy by changing a ratio of the length of the major axis to the length of the minor axis, and may have an angle.

According to the example embodiment, when a size of the anisotropic filter kernel to be used is set as N, the length of the major axis of the two-dimensional anisotropic Gaussian function is set as $\sigma_x = N$, the length of the minor axis thereof is set as $\sigma_y = (1 - C(x, y))N$, and the angle is set as $$\theta = \tan\left(\frac{Dy}{Dx}\right).$$

In this way, it is possible to generate a kernel of a two-dimensional anisotropic Gaussian function type based on the structure direction and the signal coherence.

$$f(x, y) = Ae^{-(a(x-x_0)^2 + 2b(x-x_0)(y-y_0) + c(y-y_0)^2)} \qquad \text{Equation (9)}$$

where, $$a = \frac{\cos^2\theta}{2\sigma_x^2} + \frac{\sin^2\theta}{2\sigma_y^2}$$

$$b = -\frac{\sin 2\theta}{4\sigma_x^2} + \frac{\sin 2\theta}{4\sigma_y^2}$$

$$c = \frac{\sin^2\theta}{2\sigma_x^2} + \frac{\cos^2\theta}{2\sigma_y^2}$$

Such a filter kernel may be generated through repetitive calculation for each pixel. However, in order to reduce the amount of calculation, after an array of filter kernels for structure directions and signal coherences is previously generated, a filter kernel corresponding to the structure direction and the signal coherence that are obtained for each signal may be selected by referring to the previously generated structure directions and signal coherences.

In the third step of the example embodiment, after obtaining the filter kernel that reflects the structure direction and the signal coherence at each pixel, an anisotropic-smoothed intermediate image is obtained by performing the anisotropic smoothing through filtering on the image. In this case, when noise in the image is large, since there is a large error in the initially obtained structure direction and signal coherence for each pixel, it is preferred that the anisotropic smoothing be repeatedly performed by the number of times that is determined by multiplying the sum of the estimated amounts of noise in the image and a predetermined proportional coefficient.

Figure 6:
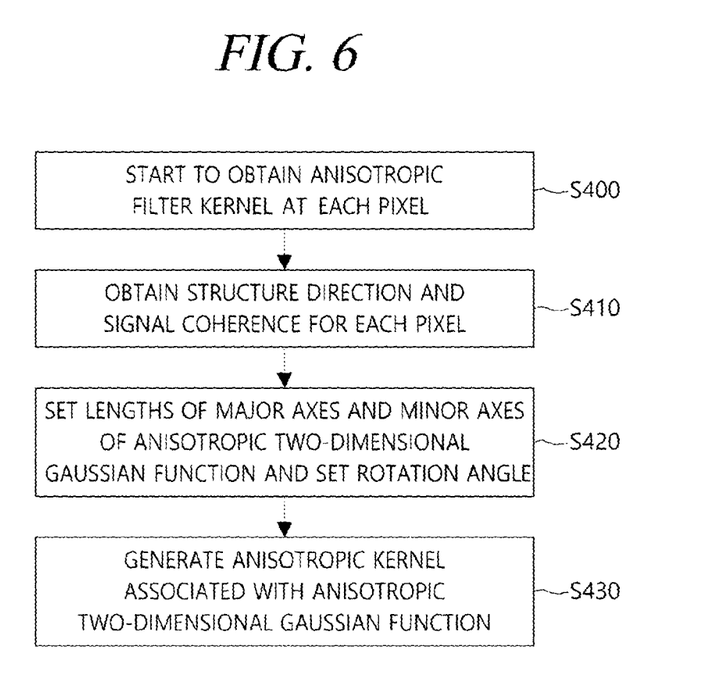
FIG. 6 shows an example processing flow of generating an anisotropic kernel using a two-dimensional anisotropic Gaussian function, in accordance with various embodiments described herein.
Figure 7:
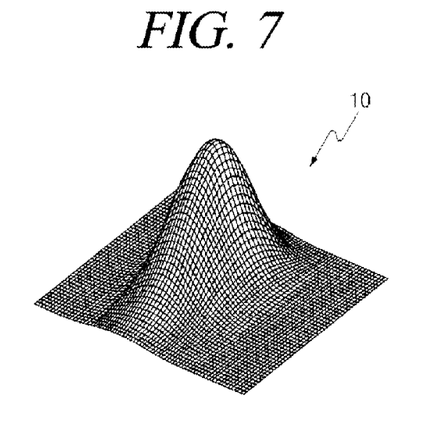
FIG. 7 shows an example anisotropic kernel that is generated using a two-dimensional anisotropic Gaussian function, in accordance with various embodiments described herein.

FIG. 6 shows a processing flow of generating an anisotropic kernel using a two-dimensional anisotropy Gaussian function. An example of the anisotropic kernel that is generated using the two-dimensional anisotropic Gaussian function may be seen (see FIG. 7).

The fourth step in the example embodiment is a step of performing anisotropic smoothing that reflects the amount of noise at each pixel. In the fourth step, after the structure direction and the signal coherence at each pixel are obtained from the image obtained in the third step and an anisotropic filter kernel corresponding to the obtained structure direction and signal coherence is obtained, filtering that reflects the filter kernel and noise statistics of the corresponding pixel is performed on an original image to obtain a final noise-suppressed image.

In the fourth step, most importantly, an additional weight that reflects the noise statistics is applied to surrounding pixels within a range of the anisotropic filter kernel. By doing this, filtering is not performed on surrounding pixels beyond a range of the noise statistics, and as a result, it is possible to preserve a structure component.

In the fourth step, as the method of applying the additional weight that reflects the noise statistics to the surrounding pixels within the range of the anisotropic filter kernel, any method may be used as long as it satisfies a principle of preserving the structure component. In the example embodiment, two preferred examples will be described to help understanding of such a principle.

In the first preferred example, it is assumed that the central pixel on which the anisotropic filter kernel is located is [x, y], the estimated amount of noise at the central pixel is $\sigma_n[x, y]$, a pixel value of the smoothed intermediate image, which is obtained in the third step, at the central pixel is $I_s[x, y]$, a position of the surrounding pixel, which is spaced apart from the central pixel within the range of the kernel by i pixels in an x-axis direction and j pixels in a y-axis direction, is [x+i, y+j], and a pixel value of the original image in the position of the surrounding pixel is I[x+i, y+j]. Under such a condition, a ratio is obtained by dividing an absolute value of a difference value between I[x+i, y+j] and $I_s[x, y]$ by the estimated amount of noise $\sigma_n[x, y]$, and a value obtained by dividing the sum of the obtained ratio and a predetermined constant β by 1 is applied as a weight for the corresponding surrounding pixel. In the example, a calculation expression of the weight may be expressed as Equation (10).

$$W_{x,y}(i, j) = \frac{1}{\beta + \frac{|I[x+i, y+j] - I_S[x, y]|}{\sigma_n[x, y]}}$$ Equation (10)

Figure 8:
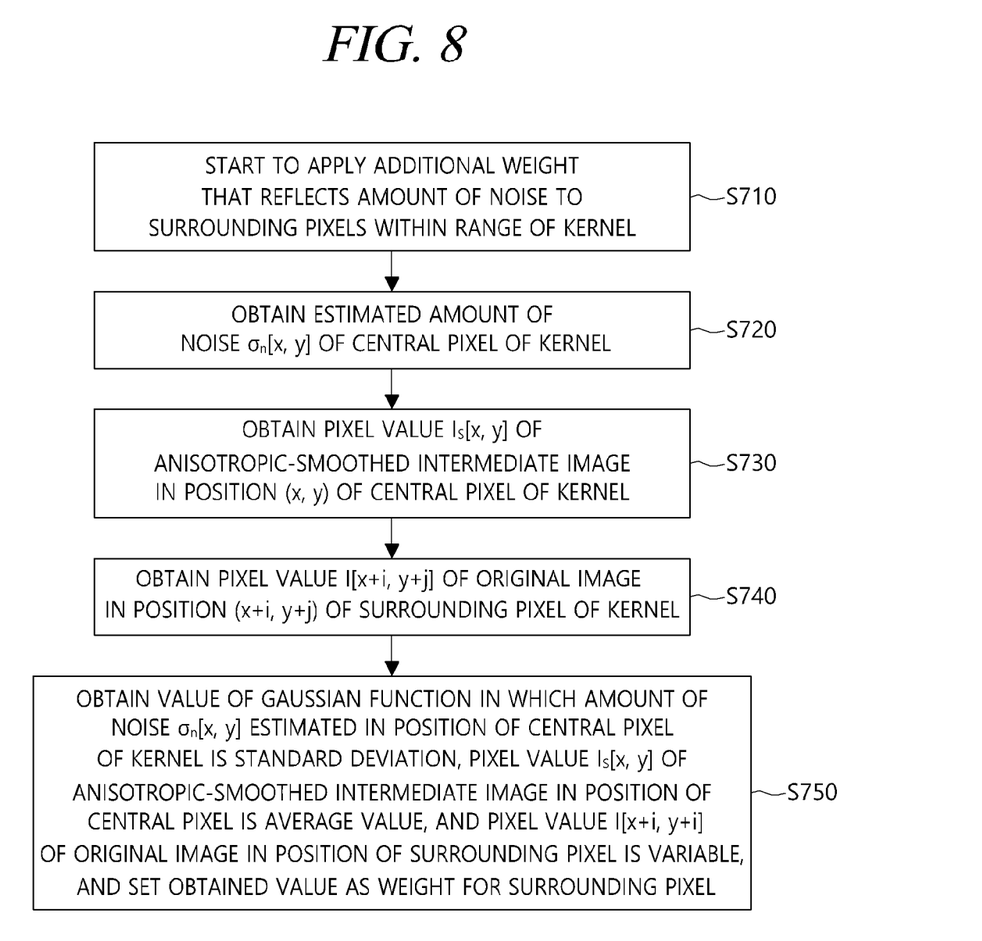
FIG. 8 shows an example processing flow of applying a weight that reflects an amount of noise to surrounding pixels within a kernel by using a Gaussian function, in accordance with various embodiments described herein.

In the second preferred example, a value of the Gaussian function in which the estimated amount of noise $\sigma_n[x, y]$ at the position [x, y] of the central pixel of the kernel is a standard deviation, the pixel value $I_s[x, y]$ of the anisotropic-smoothed intermediate image at the central pixel is an average value, and the pixel value I[x+i, y+j] of the original image in the position [x+i, y+j] of the surrounding pixel, which is spaced apart from the central pixel of the kernel by i pixels in the x-axis direction and j pixels in the y-axis direction, is a variable is obtained. The obtained value of the Gaussian function is set as a weight for the position [x+i, y+j] of the surrounding pixel.

In the example, the calculation expression of the weight may be expressed as Equation (11).

$$W_{x,y}(i, j) = \exp\left(\frac{-(I[x+i, y+j] - I_S[x, y])^2}{2\sigma_n[x, y]^2}\right)$$ Equation (11)

Equation (12) represents a procedure of performing filtering with the anisotropic kernel $K_{x,y}[i, j]$ by using the weight $W_{x,y}(i, j)$ that reflect the amount of noise according to the above-stated methods.

$$I_{sn}[x,y] = A_{x,y} \Sigma_{-N/2}^{N/2} \Sigma_{-N/2}^{N/2} I[x+i, y+j] W_{x,y}(i,j) K_{x,y}[i, j]$$ Equation (12)

where, $I_{sn}[x, y]$ is a pixel value obtained through filtering at the central pixel of the kernel, $A_{x, y}$ is a correction coefficient that allows the sum of kernels to be 1, and N is a size of the kernel.

By performing the anisotropic smoothing in consideration of the noise statistics, it is possible to selectively suppressing the noise component while preserving the structure component of the signal.

In this case, when noise within the image is large, the noise suppressing effect may not be sufficiently exhibited. Accordingly, it is preferred that the anisotropic smoothing filtering in consideration of the noise statistics be repeatedly performed by the number of times determined by multiplying the sum of the estimated amounts of noise within the image obtained from the original image and a predetermined proportional coefficient. In this case, since magnitude of noise is reduced through filtering, a value obtained by multiplying a predetermined reduction coefficient and the estimated amount of noise of the preceding filtering is preferably used as the estimated amount of noise for each pixel whenever the filtering is repeated.

Meanwhile, when the medical image is observed with naked eye, it is natural to allow a small amount of noise components existing in a natural state to be included in the image. Accordingly, it may be possible to provide, as a final output, an image obtained by mixing a filtering result value $I_{sn}[xy]$ with the pixel value I[x, y] of the original image by a predetermined ratio α, as expressed by Equation (13).

$$I_{sn}[x,y] = (1-\alpha)I_{sn}[x,y] + \alpha I[x,y]$$ Equation (13)

As mentioned above, the present disclosure has been described in conjunction with the limited example embodiments with reference to the drawings, but is not limited thereto. It should be apparent to those skilled in the art that the example embodiments can be changed and modified in various manners without departing from the technical spirit of the present disclosure and the appended claims.

I claim:

1. A method of reducing noise in a medical image, the method comprising:
   a step of estimating the amount of noise in at each pixel position of an image by using a look-up table that is previously stored in order to suppress noise in the medical image;
   a step of extracting a first signal structure direction and a first signal coherence at each pixel position;
   a step of obtaining a first anisotropic smoothing filter kernel that reflects the extracted signal structure direction and the signal coherence;
   a step of obtaining an anisotropic-smoothed intermediate image by performing filtering using the first anisotropic smoothing filter kernel; and
   a step of extracting a second signal structure direction and a second signal coherence at each pixel of the anisotropic-smoothed intermediate image, and obtaining a second anisotropic filter kernel that reflects the second signal structure direction and the second signal coherence, and performing filtering on an original image by applying an additional weight that reflects the estimated amount of noise in the position of each pixel to surrounding pixels within a range of the filter kernel.

2. The method of reducing noise in the medical image of claim 1,
   wherein the look-up table that previously stores physical properties of an image capturing device is a two-dimensional look-up table that has two terms including a radiation dose for an object during irradiation of X-ray and a signal average value at each pixel in an image, and provides a noise standard deviation at each pixel by inputting a radiation dose value which is provided from the image capturing device and a signal average value at each pixel in the image.

3. The method of reducing noise in the medical image of claim 2,
   wherein when the radiation dose value is not provided from the image capturing device, the radiation dose value is generated by referring to the look-up table that previously stores information including an X-ray tube voltage, the product of a tube current and radiation time, a distance between an X-ray focal point and a detector, and a used X-ray energy filter.

4. The method of reducing noise in the medical image of claim 1,
   wherein in the step of extracting the signal structure direction and the signal coherence at each pixel position, the signal structure direction is determined as a vertical direction of a gradient vector that is normalized at each pixel, and the signal coherence is determined by obtaining absolute values of gradient values of the normalized gradient vector and a vertical direction vector of the gradient vector and dividing a difference value between the absolute values of the gradient values by the sum of the absolute values.

5. The method of reducing noise in the medical image of claim 1,
wherein in the step of extracting the signal structure direction and the signal coherence at each pixel position, the signal structure direction is determined as a second eigenvector of the Hessian matrix for each pixel, and the signal coherence is determined by obtaining absolute values of two eigenvalues of the Hessian matrix and dividing a difference value between the absolute values of the two eigenvalues by the sum of the absolute values.

6. The method of reducing noise in the medical image of claim 4,
wherein in the step of extracting the signal structure direction and the signal coherence at each pixel position, the signal structure direction and the signal coherence are determined as the signal structure direction and the signal coherence according to claim 4 when a ratio of an absolute value of a gradient value obtained at each pixel to an absolute value of a first eigenvalue of the Hessian matrix is obtained and the obtained ratio is greater than a predetermined threshold value, and the signal structure direction and the signal coherence are determined as the signal structure direction and the signal coherence according to claim 5 when the ratio is smaller than the predetermined threshold value.

7. The method of reducing noise in the medical image of claim 1,
wherein in the step of obtaining the anisotropic smoothing filter kernel that reflects the signal structure direction and the signal coherence that are extracted at each pixel, a kernel that follows a two-dimensional anisotropic Gaussian function using the structure direction and the signal coherence is obtained, and lengths of a major axis and a minor axis of the anisotropic Gaussian function are respectively determined as a size of the kernel and a value obtained by multiplying the size of the kernel and the signal coherence, and a rotation angle of the anisotropic Gaussian function is determined as the structure direction.

8. The method of reducing noise in the medical image of claim 1,
wherein in the step of obtaining the anisotropic-smoothed intermediate image by performing filtering using the first anisotropic smoothing filter kernel, anisotropic smoothing filtering is repeatedly performed by the number of times that is determined by multiplying a predetermined proportional coefficient and the sum of the estimated amounts of noise in the respective pixels in the image in claim 1.

9. The method of reducing noise in the medical image of claim 1,
wherein in the step of applying the additional weight that reflects the estimated amount of noise in the position of each pixel to the surrounding pixels within the range of the filter kernel, a ratio is obtained by dividing an absolute value of a difference value between a pixel value of the anisotropic-smoothed intermediate image at the central pixel of the kernel and the pixel value of the original image at surrounding pixel by the estimated amount of noise, and a value obtained by dividing the sum of the ratio and a predetermined constant β by 1 is applied as a weight for the surrounding pixel.

10. The method of reducing noise in the medical image of claim 1,
wherein in the step of applying the additional weight that reflects the estimated amount of noise at each pixel position to the surrounding pixels within the range of the filter kernel, a value of the Gaussian function in which the estimated amount of noise at the central pixel of the kernel is set as a standard deviation, the pixel value of the anisotropic-smoothed intermediate image is set as an average value, and the pixel value of the original image at the surrounding pixel is set as a variable is obtained, and the obtained value is set as the weight for the surrounding pixel.

11. The method of reducing noise in the medical image of claim 1,
wherein in the step of performing filtering on the original image by applying the additional weight that reflects the estimated amount of noise at each pixel position to the surrounding pixels within the range of the filter kernel and outputting the filtered image as a final output, the filtering is repeatedly performed by the number of times determined by multiplying a predetermined proportional coefficient and the sum of the estimated amounts of noise for the respective pixels in the image, which are obtained from the original image, and a value obtained by multiplying a predetermined reduction coefficient and the estimated amount of noise of the preceding filtering is used as the estimated amount of noise at each pixel whenever the filtering is repeated.

12. The method of reducing noise in a medical image of claim 1,
wherein in the step of performing filtering on the original image by applying the additional weight that reflects the estimated amount of noise at each pixel position to the surrounding pixels in the range of the filter kernel and outputting the filtered image as a final output, a small amount of noise existing in a natural state is included in the original image by mixing a filtering result value $I_{sn}[x, y]$ at each pixel and a pixel value $I[x, y]$ of the original image by a predetermined ratio.

13. The method of reducing noise in the medical image of claim 5,
wherein in the step of extracting the signal structure direction and the signal coherence at each pixel position, the signal structure direction and the signal coherence are determined as the signal structure direction and the signal coherence according to claim 4 when a ratio of an absolute value of a gradient value obtained at each pixel to an absolute value of a first eigenvalue of the Hessian matrix is obtained and the obtained ratio is greater than a predetermined threshold value, and the signal structure direction and the signal coherence are determined as the signal structure direction and the signal coherence according to claim 5 when the ratio is smaller than the predetermined threshold value.

* * * * *